(12) United States Patent
Hwang et al.

(10) Patent No.: US 8,809,401 B2
(45) Date of Patent: Aug. 19, 2014

(54) COMPOSITION WITH IMPROVED SKIN PENETRATION FOR TRANSDERMAL DELIVERY OF TOLTERODINE

(75) Inventors: Yong Youn Hwang, Gyeonggi-do (KR); Won-Jae Choi, Seoul-si (KR); Jae-Sun Kim, Gyeonggi-do (KR); Yeo-Jin Park, Seoul-si (KR); Joon-Gyo Oh, Gyeonggi-do (KR); Bong-Yong Lee, Seoul-si (KR); Hae-In Rhee, Gyeonggi-do (KR); Jong-Seob Im, Gyeonggi-do (KR)

(73) Assignee: SK Chemicals Co., Ltd., Seongnam-si, Gyeonggi-do (KR)

(*) Notice: Subject to any disclaimer, the term of this patent is extended or adjusted under 35 U.S.C. 154(b) by 60 days.

(21) Appl. No.: 13/579,824

(22) PCT Filed: Feb. 17, 2011

(86) PCT No.: PCT/KR2011/001064
§ 371 (c)(1),
(2), (4) Date: Nov. 1, 2012

(87) PCT Pub. No.: WO2011/102657
PCT Pub. Date: Aug. 25, 2011

(65) Prior Publication Data
US 2013/0046026 A1 Feb. 21, 2013

(30) Foreign Application Priority Data

Feb. 18, 2010 (KR) .................. 10-2010-0014554

(51) Int. Cl.
*A61K 31/05* (2006.01)
(52) U.S. Cl.
USPC ............ 514/741; 424/443; 424/447; 424/449
(58) Field of Classification Search
USPC .......................... 514/741; 424/443, 447, 449
See application file for complete search history.

(56) References Cited

U.S. PATENT DOCUMENTS

| | | | | |
|---|---|---|---|---|
| 5,298,257 | A * | 3/1994 | Bannon et al. | 424/449 |
| 6,310,103 | B1 * | 10/2001 | Aberg | 514/741 |
| 6,770,295 | B1 * | 8/2004 | Kreilgård et al. | 424/457 |
| 6,783,769 | B1 | 8/2004 | Arth et al. | |
| 7,008,637 | B2 * | 3/2006 | Jacobsen et al. | 424/449 |
| 2013/0046025 | A1 * | 2/2013 | Hwang et al. | 514/626 |

* cited by examiner

*Primary Examiner* — My-Chau T Tran
(74) *Attorney, Agent, or Firm* — Edwards Wildman Palmer LLP; Kongsik Kim

(57) ABSTRACT

Disclosed is a composition for transdermal administration containing tolterodine. The composition comprises lidocaine or a pharmaceutically acceptable salt thereof to achieve enhanced skin penetration. The composition enhances the skin penetration of tolterodine. Therefore, a successful commercial application of a tolterodine-containing transdermal preparation based on the composition can be expected.

4 Claims, 1 Drawing Sheet

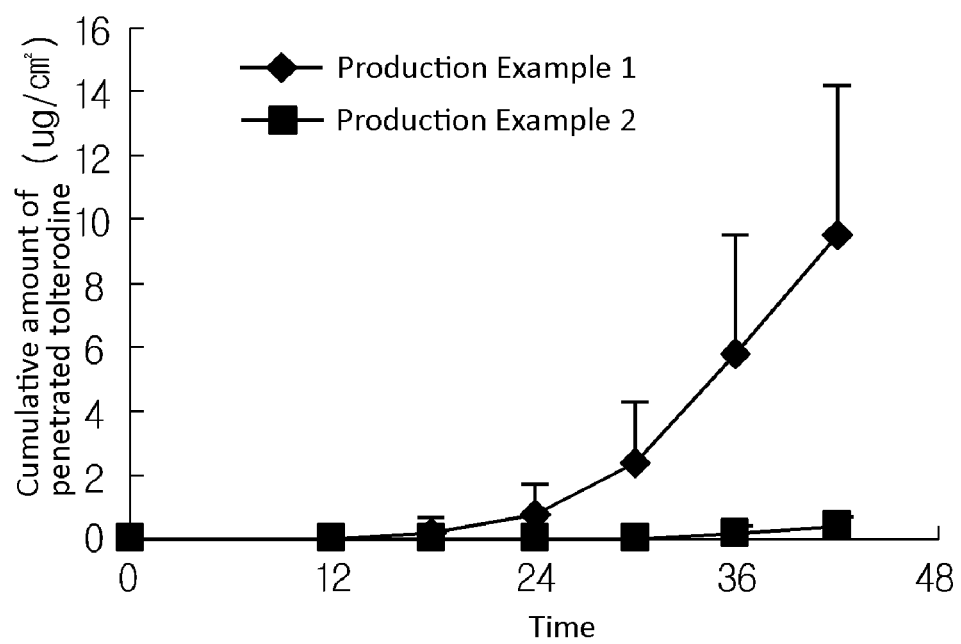

COMPOSITION WITH IMPROVED SKIN PENETRATION FOR TRANSDERMAL DELIVERY OF TOLTERODINE

CROSS-REFERENCES TO RELATED APPLICATIONS

This application is a U.S. national phase application, pursuant to 35 U.S.C. §371, of PCT/KR2011/001064, filed Feb. 17, 2011, designating the United States, which claims priority to Korean Application No. 10-2010-0014554, filed Feb. 18, 2010. The entire contents of the aforementioned patent applications are incorporated herein by this reference.

TECHNICAL FIELD

The present disclosure relates to a composition for transdermal administration which contains tolterodine as an active ingredient and improves the skin penetration of tolterodine.

BACKGROUND ART

An overactive bladder refers to a disease with symptoms of urinary frequency, urinary urgency or urgent urinary incontinence. Urinary frequency is a need to urinate more than usual, mostly more than eight times a day, and still having the desire to urinate even when the bladder is not full. Urinary urgency is a sudden strong uncontrollable urge to urinate. Urgent urinary incontinence is a condition of involuntary leakage of urine. Excessively frequent contraction of the smooth muscle of the bladder (detrusor muscle) is presumed to be a cause of overactive bladder. That is, the bladder muscle contracts more frequently than normal or when unnecessary, causing a sudden uncontrollable urge to urinate before the bladder is full. Most causes of such bladder muscle contraction remain unknown. In some cases, symptoms of an overactive bladder develop due to problems in neurotransmission from the brain to the bladder or neuronal damage arising from surgery or parturition. For males, overactive bladder diseases may be accompanied by prostatic hyperplasia.

Overactive bladder can lead to lack of sleep, reduced work efficiency, avoidance of sexual life, and depression. Overactive bladder can eventually lead to a poor quality of life due to lack of information concerning overactive bladder and feelings of shame.

U.S. Pat. No. 5,382,600 discloses (substituted) 3,3-diphenylpropylamines useful for the treatment of urinary incontinence. Particularly, this patent describes that 2-[(1R)-3-(diisopropylamino)-1-phenylpropyl)-4-methylphenol, which has a general name of tolterodine and is known as N,N-diisopropyl-3-(2-hydroxy-5-methylphenyl)-3-phenylpropylamine, is useful for the treatment of urinary incontinence. Tolterodine is currently used in the form of an acid addition salt with a pharmaceutically acceptable acid. A tolterodine acid addition salt commercially available for the treatment of overactive bladder is tolterodine tartrate.

Presently, anticholinergic drugs account for most therapeutic drugs for overactive bladder. However, anticholinergic drugs have side effects, such as dry mouth, constipation and disturbance of consciousness, which serve as great barriers to patients with overactive bladder in need of long-term administration. Particularly, the administration of anticholinergic drugs increases the risk of urinary obstruction in patients with prostatic hyperplasia and is prohibited in patients with dementia and patients with glaucoma. Under these circumstances, there is a need to develop a novel therapeutic drug or a pharmaceutical drug delivery system that can improve the quality of life. One approach to reduce the side effects of a therapeutic drug for overactive bladder is to biopharmaceutically control the blood level of the drug above a minimum effective concentration and below a concentration at which the side effects occur. For this approach, studies on sustained-release pharmaceutical drug delivery systems are much underway. Currently commercially available dosage forms of tolterodine are film-coated tablets containing 1 mg, 2 mg or 4 mg of tolterodine L-tartrate that is released in the gastrointestinal tract upon administration.

Transdermal drug delivery systems are technologies by which drugs are absorbed through the skin. Transdermal drug delivery systems have particular advantages of reduced side effects, particularly, in the gastrointestinal tract, bypass of hepatic first pass and enhanced convenience of administration to patients due to their ability to maintain the concentration of drugs at a constant level compared to other drug delivery systems. Therefore, transdermal drug delivery systems can be considered an optimal system to reduce the side effects of therapeutic drugs for overactive bladder and enhance the convenience of administration to patients.

U.S. Pat. No. 6,517,864 discloses that transdermal administration of tolterodine is useful for the treatment of overactive bladder. Particularly, this patent discloses that small doses and short half-life make tolterodine favorable as a drug for transdermal administration and tolterodine in the form of free base is more effective in skin penetration than tolterodine in the form of an acid addition salt with a pharmaceutically acceptable acid. However, the skin absorption rate (permeability) of tolterodine is very low, which needs to be increased.

DISCLOSURE

Technical Problem

The present disclosure is designed to solve the problems of the prior art, and therefore it is an object of the present disclosure to provide a composition for transdermal administration of tolterodine with improved skin penetration. Tolterodine is administered transdermally for the purposes of reducing the side effects of the therapeutic drug for overactive bladder and improving the convenience of administration to patients while maintaining the blood concentration of tolterodine at a constant level. In this case, the skin permeability of tolterodine should be above a predetermined level.

Technical Solution

In order to achieve the object of the present disclosure, there is provided a composition for transdermal administration which comprises tolterodine as an active ingredient and lidocaine or a pharmaceutically acceptable salt thereof to achieve improved skin penetration of tolterodine.

In the course of research aimed at developing a composition for transdermal administration of tolterodine, the inventors of the present disclosure have found a phenomenon that lidocaine markedly enhances the skin penetration of tolterodine. The present disclosure has been accomplished based on this finding.

Lidocaine used in the composition of the present disclosure is in the form of free base or an acid addition salt with a pharmaceutically acceptable salt.

In the present disclosure, the lidocaine in the form of free base is used in an amount of 1 to 300 parts by weight, preferably 10 to 200 parts by weight, more preferably 50 to 200 parts by weight, based on 100 parts by weight of tolterodine.

The use of the lidocaine in an amount of less than 1 part by weight is not sufficient in effectively enhancing the skin penetration of tolterodine. Meanwhile, the use of the lidocaine in an amount exceeding 300 parts by weight does not contribute to a further enhancement in skin penetration and disadvantageously causes a reduction in the adhesive strength of a patch in the form of a matrix to be produced.

The composition of the present disclosure may use either tolterodine free base or an acid addition salt of tolterodine. The use of tolterodine free base is more preferred taking into consideration suitable physiochemical properties of the drug for transdermal absorption.

The composition for transdermal administration according to the present disclosure can be prepared into formulations, for example, a patch, a liquid and an ointment. A patch is most preferred.

The patch may use a suitable base known in the art, for example, an excipient assisting in the transdermal absorption of the composition or an adhesive assisting in the adhesion of the composition to the skin. Other additives may be added to promote skin penetration or relieve skin irritation so long as the object of the present disclosure is not impaired.

A solvent may be used to dissolve the drug in the course of producing the patch. Examples of such solvents include ethanol, isopropanol, propylene glycol and ethyl acetate. The solvent is typically used in an amount of 50 to 500 parts by weight, based on 100 parts by weight of tolterodine. The solvent may be removed in the course of preparing the composition for transdermal administration. Alternatively, the solvent may remain in the final composition for transdermal administration. In this case, the residual amount of the solvent can be suitably adjusted by the International Conference on Harmonization (ICH) guidelines.

The composition for transdermal administration according to the present disclosure may use a pressure sensitive adhesive (PSA) for medical applications as an adhesive polymer. The adhesive polymer may be based on water or organic solvent. Examples of preferred adhesive polymers include: acrylic adhesives, such as acrylate polymers and vinyl acetate-acrylate copolymers; polyisobutylene; polystyrene; polybutadiene; copolymers thereof, such as synthetic and natural rubbers; and silicone-based adhesives. These adhesive polymers may be used alone or as a mixture of two or more thereof.

The content of the adhesive polymer is preferably from 500 to 5,000 parts by weight, based on 100 parts by weight of tolterodine. If the adhesive polymer is used in an amount of less than 500 parts by weight, a homogeneous phase cannot be formed as a result of mixing with the other additives, making it impossible to produce a patch and causing problems such as reduced adhesive strength. Meanwhile, if the adhesive polymer is used in an amount exceeding 5,000 parts by weight, the relatively low contents of tolterodine and the other additives preclude the individual ingredients to sufficiently play their roles, resulting in a marked decrease in the absorption of the drug.

The dosage of the composition of the present disclosure may vary depending on the age, weight, sex and health of patients being treated, the mode of administration, and severity of the disease being treated.

Advantageous Effects

The composition for transdermal administration according to the present disclosure greatly increases the skin penetration of tolterodine. Therefore, the content of tolterodine in the composition can be reduced. In addition, the skin permeability of tolterodine is above a predetermined level. Therefore, a successful commercial application of a tolterodine-containing transdermal preparation based on the composition of the present disclosure can be expected.

DESCRIPTION OF DRAWINGS

FIG. 1 is a graph showing a difference in the amount of tolterodine penetrating the skin depending on the presence or absence of lidocaine.

BEST MODE

The present disclosure will be explained in detail with reference to the following examples to assist in a further understanding of the present disclosure. However, these examples may be embodied in various different forms and should not be construed as limiting the scope of the present disclosure. The examples are provided to more fully explain the present disclosure to those having ordinary knowledge in the art to which the present disclosure pertains.

EXAMPLES

Production Examples 1-2

Production of Tolterodine-Containing Patches

In accordance with the composition shown in Table 1, a solution of tolterodine free base and lidocaine free base in ethanol was mixed with the acrylic pressure sensitive adhesive for about 10 min. The mixture was allowed to stand at room temperature for at least 4 hr to remove bubbles. The resulting mixture was applied to a thickness of 400 μm onto a silicone-coated polyester film at a rate of 0.5 m/min using an applicator, dried in a hot-air dryer at 80° C. for 15 min, followed by lamination with a polyethylene film to produce a tolterodine-containing patch (Production Example 1). A patch was produced in the same manner as described above, except that lidocaine free base was not used (Production Example 2).

TABLE 1

|  | Tolterodine free base (g) | Lidocaine free base (g) | Acrylic pressure sensitive adhesive (g) |
| --- | --- | --- | --- |
| Production Example 1 | 1.32 | 1.32 | 12.2 |
| Production Example 2 | 1.32 | 0.00 | 12.2 |

Test Example 1

Skin Penetration Test

Each of the patches produced in Production Examples 1 and 2 was cut to a size of 1 cm×1 cm. The specimen was attached to a skin piece excised from a pig, placed on a Franz cell, and dipped in a receptor solution (0.05 M isotonic phosphate buffer solution, pH=7.4, temperature=32° C., stirring rate=300 rpm) at uniform time intervals for 42 hr. The tolterodine free base penetrated into the receptor solution was quantified by high-performance liquid chromatography. The quantification was repeated to calculate the cumulative amount of the tolterodine. The amounts of the tolterodine penetrating the skin depending on the absence or presence of lidocaine were measured. The results are shown in Table 2 and FIG. 1.

TABLE 2

| Cumulative amount of tolterodine penetrating (μg/cm²) | Production Example 1 (Patch containing lidocaine free base) | Production Example 2 (Patch containing no lidocaine free base) |
| --- | --- | --- |
| 0 hr | 0.00 | 0.00 |
| 12 hr | 0.00 | 0.00 |
| 18 hr | 0.23 | 0.00 |
| 24 hr | 0.80 | 0.00 |
| 30 hr | 2.37 | 0.00 |
| 36 hr | 5.82 | 0.19 |
| 42 hr | 9.50 | 0.37 |

As can be seen from the results in Table 2, lidocaine is effective in promoting the skin penetration of tolterodine.

What is claimed is:

1. A composition for transdermal administration comprising tolterodine, characterized in that the composition comprises lidocaine or its pharmaceutically acceptable salt to enhance the skin penetration of tolterodine, wherein the lidocaine or its pharmaceutically acceptable salt is used in an amount of 1 to 300 parts by weight, based on 100 parts by weight of the tolterodine.

2. A composition for transdermal administration comprising tolterodine, characterized in that the composition comprises lidocaine or its pharmaceutically acceptable salt to enhance the skin penetration of tolterodine, wherein the composition comprises 100 parts by weight of the tolterodine, 500 to 5,000 parts by weight of an adhesive acrylate copolymer, and 1 to 300 parts by weight of the lidocaine or its pharmaceutically acceptable salt.

3. The composition for transdermal administration according to claim 1, wherein the tolterodine is in the form of free base.

4. The composition for transdermal administration according to claim 2, wherein the tolterodine is in the form of free base.

* * * * *